United States Patent [19]

Shah et al.

[11] 4,415,549
[45] Nov. 15, 1983

[54] TOOTHPASTES WITH REDUCED SALINITY
[75] Inventors: Nutan B. Shah, New Rochelle, N.Y.; Marvin K. Cook, Port Charlotte, Fla.
[73] Assignee: Richardson-Vicks Inc., Wilton, Conn.
[21] Appl. No.: 378,889
[22] Filed: May 17, 1982
[51] Int. Cl.$^3$ .......................... A61K 9/16; A61K 9/18
[52] U.S. Cl. ....................................... 424/52; 424/49; 424/54
[58] Field of Search ..................................... 424/49–58
[56] References Cited

U.S. PATENT DOCUMENTS

| Re. 30,675 | 7/1981 | Schole | 424/54 |
|---|---|---|---|
| 3,122,483 | 2/1964 | Rosenthal | 424/55 |
| 3,699,221 | 10/1972 | Schole et al. | 424/54 |
| 3,988,434 | 10/1976 | Schole et al. | 424/54 |
| 4,137,303 | 1/1979 | Gaffar et al. | 424/52 |
| 4,175,120 | 11/1979 | Schole et al. | 424/54 |
| 4,224,310 | 9/1980 | Shah | 424/49 |
| 4,283,385 | 8/1981 | Dhabhar et al. | 424/52 |
| 4,357,318 | 11/1982 | Shah et al. | 424/52 |

FOREIGN PATENT DOCUMENTS

| 54-26339 | 2/1979 | Japan . |
| 56-65813 | 6/1981 | Japan . |
| 1567307 | 5/1980 | United Kingdom . |

OTHER PUBLICATIONS

Marvin Cook et al. "Glycyrrhizin" Chap. 19, pp. 211–215 (1974) ACS Sympos. Sweeteners Mtg. Dallas, Texas, Apr. 9–13 (1903) pub. 1974 AVI Westport Conn.
Marvin Cook (1971) Drug Cosmetic Ind. 109 No. 10, 50, 52 138–140 Licorice Root Derivatives for Use in Cosmetic Products.
Marvin Cook (1971) Flavor Ind. 2 No. 3: 155–156 Flavor Creation.
Marvin Cook (1955) Drug Cosmetic Ind. 76 No. 5: 624–625 Pharmaceutical Flavoring.
Marvin Cook (1958) Drug Cosmetic Ind. 82 (3): 314–316 Modern Toothpaste Manufacture.
Dedieu et al. Chem Abstr. 94#36132z(1981) of Brit. 1,567,307 May 14, 1980 "Salts of Glycyrrhizinic Acid".
Macandrews & Forbes Chem. Abstr. 95#120993t(1981) of Jpn. Kokai Tokkyo Koho 81 65813 Jun. 3, 1981 "Toothpastes Containing Glycyrrhizin and Menthol".
Sato et al. Chem. Abstr. 91#9357h(1979) of Jpn. Kokai Tokkyo Koho 7926339 Feb. 27, 1979 "Saccharin-Free Dentifrices".

*Primary Examiner*—Shep K. Rose
*Attorney, Agent, or Firm*—Salvatore R. Conte

[57] ABSTRACT

Toothpaste compositions having monoammonium glycyrrhizinate, strontium disodium ethylenediamine tetraacetate and sodium fluoride or sodium monofluorophosphate.

9 Claims, No Drawings

TOOTHPASTES WITH REDUCED SALINITY

FIELD OF THE INVENTION

This invention relates to toothpaste compositions containing strontium disodium ethylenediamine tetraacetate and, as the source of available fluoride, either sodium fluoride or sodium monofluorophosphate or both, to which is added a minor amount of monoammonium glycyrrhizinate to substantially reduce or suppress salinity.

BACKGROUND OF THE INVENTION

It has heretofore been known to improve oral hygiene by applying to teeth certain non-fluoride containing dentifrice compositions containing a particular strontium chelate, namely strontium disodium ethylenediamine tetraacetate, for example, as disclosed in U.S. Pat. Nos. 3,699,221 and 3,988,434. However, a problem associated with such dentifrices when strontium chloride is used as a reactant to form said strontium disodium ethylenediamine tetraacetate in situ is an unacceptable saltiness or metallic tastiness in the product. Amelioration of this problem by the addition of flavoring and/or sweetening agents has not always been achieved. Recently, in U.S. Pat. No. 4,224,310 a particular method of forming said strontium disodium ethylenediamine tetraacetate in situ is stated to avoid the salty or metallic taste problem in non-fluoride containing dentifrices.

However, even with toothpastes containing strontium disodium ethylenediamine tetraacetate which have been formulated in such a way as to be relatively "salt-free" or "clean" tastewise, upon subsequent inclusion of either sodium fluoride or sodium monofluorophosphate as a source of available anti-caries fluoride, the resulting product inherently acquires an unacceptable salty taste due to the presence of such fluoride salt.

BRIEF DESCRIPTION OF THE INVENTION

It has now been discovered that a water-containing toothpaste composition which contains strontium disodium ethylenediamine tetraacetate (Sr-diNa-EDTA) plus sodium fluoride and/or sodium monofluorophosphate can be formulated such that the problem of saltiness in the resulting product is substantially ameliorated and a highly acceptable pleasant tasting product is obtained. This is accomplished by incorporation of a minor amount of monoammonium glycyrrhizinate (also known as monoammonium glycyrrhizate), a licorice root derivative, into the toothpaste composition.

DETAILED DESCRIPTION OF THE INVENTION

A wide variety of dentifrice compositions containing sodium fluoride and/or sodium monofluorophosphate to prevent tooth decay have been known for some time (usual fluorine content: 200 to 1000 ppm). Similarly, the use of strontium disodium ethylenediamine tetraacetate in dentifrices is also known to be beneficial for promoting good dental hygiene and in treating various dental disorders (see U.S. Pat. Nos. 3,699,221 and 3,988,434).

The combination of sodium fluoride and/or sodium monofluorophosphate with Sr-diNa-EDTA in the same toothpaste, however, presents a taste problem to the user due to saltiness. The immediate and lingering salinity is obtrusive and influences unfavorably the overall flavor effect of the toothpaste, even with conventional sweeteners and flavoring agents added. This serious drawback, from the viewpoint of consumer acceptance, is substantially overcome, in accordance with this invention, by the incorporation of at least 0.001 percent by weight of monoammonium glycyrrhizinate into the fluoride/Sr-diNa-EDTA containing toothpaste. The monoammonium glycyrrhizinate is soluble in glycerin and is readily incorporated into the toothpaste compositions by standard formulating methodology.

The preferred amount of monoammonium glycyrrhizinate is from about 0.005 to about 0.025 percent by weight, and most preferably from about 0.005 to about 0.0125 percent by weight, based on the total weight of the toothpaste, although much higher amounts, for example, up to about 0.5 percent by weight, may be effectively employed. At high concentrations, however, the characteristic licorice flavor of the glycyrrhizinate salt may become a taste factor to be considered in addition to the reduction of taste-saltiness.

In addition to the three essential components of the subject toothpastes, namely (i) strontium disodium ethylenediamine tetraacetate, (ii) sodium fluoride, sodium monofluorophosphate or mixtures thereof, and (iii) monoammonium glycyrrhizinate, the other components of the toothpaste composition include all conventional ingredients such as polishing agents or abrasives, thickening agents, whitening agents, wetting agents or surfactants, flavoring agents, sweeteners, coloring agents and the like. With regard to the selection of such other components, however, it should be understood that, as taught in U.S. Pat. No. 3,699,221, toothpastes containing Sr-diNa-EDTA chelate are characterized by the substantial absence of substances which can replace strontium from the chelate. Accordingly, the toothpastes of this invention should not include those wherein any of the water-insoluble calcium, magnesium or aluminum compounds generally used as abrasives in dentifrices are present. In contrast, those dentifrices wherein an abrasive inert to the Sr-diNA-EDTA chelate are recommended, preferably silicon dioxide.

In view of the foregoing examples hereinafter, the instant invention provides a vastly improved toothpaste containing Sr-diNA-EDTA and sodium fluoride or sodium monofluophosphate or both, the improvement being due to the incorporation of a minor amount of monoammonium glycyrrhizinate. By means of this ammoniated licorice root derivative, untoward flavor effects due to excessive salinity arising from said fluoride components are markedly reduced or suppressed. In its broadest aspect, the subject invention thus provides a water-containing toothpaste comprising an effective amount of strontium disodium ethylenediamine tetraacetate for alleviating sensitivity of hyper-sensitive dentin, and effective anti-caries amount of sodium fluoride, sodium monofluorophosphate or mixtures thereof and at least 0.001 percent by weight, based on the total weight of the toothpaste, of monoammonium glycyrrhizinate.

The following Examples are designed to illustrate the practice of the present invention but not to limit the scope of the invention.

| Toothpaste Ingredients | % w/w |
| --- | --- |
| Sr—diNa—EDTA | 5.0 |
| Sodium monofluorophosphate | 0.76 |
| Insoluble sodium metaphosphate | 32.0 |
| Glycerin | 13.0 |

-continued

| Toothpaste Ingredients | % w/w |
| --- | --- |
| Sorbitol (70% solution) | 10.0 |
| Sodium ricinoleate powder | 1.2 |
| Sodium lauryl sulfate | 2.0 |
| Sodium carboxymethylcellulose | 1.5 |
| Silicon dioxide | 1.2 |
| Xanthan gum | 0.7 |
| Sodium saccharin | 0.25 |
| Methyl paraben | 0.06 |
| Propyl paraben | 0.02 |
| Color (FD&C Blue #1) | 0.001 |
| Flavor (mint oil mix) | 1.35 |
| Distilled water | 30.959 |
| | 100.000 |

This fluoride/Sr-diNa-EDTA toothpaste imparts a distinctly salty initial taste, based on subjective evaluations, which lingers for about 20–30 minutes although the minty flavor is intense and pleasing. In contrast, the same formulation absent the sodium monofluorophosphate (q.s. 100 distilled water) is neither salty to the taste upon immediate usage nor thereafter.

EXAMPLE 2

| | % w/w | | |
| --- | --- | --- | --- |
| Toothpaste Ingredients | A | B | C |
| Example 1 formulation | 99.95 | 99.9 | 99.875 |
| Monoammonium glycyrrhizinate | 0.05 | 0.1 | 0.125 |
| (10% solution) | 100.00 | 100.0 | 100.000 |

Saltiness in each of the above toothpastes, containing from 0.005 to 0.0125% w/w of monoammonium glycyrrhizinate, was absent initially and in after-taste. In each instance the flavor is rather intense but very good with the mint character, free of any licorice taste, being even richer than in Example 1.

EXAMPLE 3

Substitution of sodium fluoride for the sodium monofluorophosphate of Example 1 in amounts equivalent to provide 200, 600 and 1000 ppm of available fluoride (q.s. 100 distilled water) similarly produces toothpastes with appreciable lingering saltiness. Incorporation of 0.001, 0.005 and 0.025 w/w, respectively, of monoammonium glycyrrhizinate to such toothpastes substantially eliminates the saline tastiness without any licorice taste.

EXAMPLE 4

| Toothpaste Ingredients | A | B |
| --- | --- | --- |
| Sr—diNa—EDTA | 10.0 | 5 |
| Sodium monofluorophosphate | 0.76 | 0.76 |
| Monoammonium glycyrrhizinate | 0.007 | 0.007 |
| Silica, hydrated | 28.50 | 28.50 |
| Sorbitol (70% solution) | 27.20 | 30.20 |
| Glycerin | 7.24 | 9.24 |
| Sodium lauryl sulfate | 2.00 | 2.00 |
| Sodium ricinoleate (35% solution) | 1.43 | 1.43 |
| Sodium saccharin | 0.45 | 0.45 |
| Silica, colloidal | 0.55 | 0.55 |
| Xanthan gum | 0.40 | 0.40 |
| Methylparaben | 0.06 | 0.06 |
| Propylparaben | 0.02 | 0.02 |
| Flavor (mint oil mix) | 1.25 | 1.25 |
| Color (FD&C Blue #1) | 0.001 | 0.001 |
| Distilled water | 20.132 | 25.132 |

The formulations of this Example 4 represent further toothpastes of this invention with substantially reduced saline tastiness.

Having thus described the invention, what is claimed is:

1. A water-containing toothpaste comprising an effective amount of strontium disodium ethylenediamine tetraacetate for alleviating sensitivity of hyper-sensitive dentin, an effective anti-caries amount of sodium fluoride, sodium monofluorophosphate or mixtures thereof and at least 0.001 percent by weight, based on the total weight of the toothpaste, of monoammonium glycyrrhizinate, wherein said toothpaste is characterized by the substantial absence of substances which can replace strontium from said strontium disodium ethylenediamine tetraacetate.

2. A water-containing toothpaste comprising an effective amount of strontium disodium ethylenediamine tetraacetate for alleviating hyper-sensitive dentin, an effective anti-caries amount of sodium monofluorophosphate and from about 0.005 to about 0.5 percent by weight, based on the total weight of the toothpaste, of monoammonium glycyrrhizinate, wherein said toothpaste is characterized by the substantial absence of substances which can replace strontium from said strontium disodium ethylenediamine tetraacetate.

3. A water-containing toothpaste comprising an effective amount of strontium disodium ethylenediamine tetraacetate for alleviating hyper-sensitive dentin, an effective anti-caries amount of sodium monofluorophosphate and from about 0.005 to about 0.025 percent by weight, based on the total weight of the toothpaste, of monoammonium glycyrrhizinate, wherein said toothpaste is characterized by the substantial absence of substances which can replace strontium from said strontium disodium ethylenediamine tetraacetate.

4. A water-containing toothpaste comprising an effective amount of strontium disodium ethylenediamine tetraacetate for alleviating hyper-sensitive dentin, an effective anti-caries amount of sodium monofluorophosphate and from about 0.005 to about 0.0125 percent by weight, based on the total weight of the toothpaste, of monoammonium glycyrrhizinate, wherein said toothpaste is characterized by the substantial absence of substances which can replace strontium from said strontium disodium ethylenediamine tetraacetate.

5. A water-containing toothpaste comprising an effective amount of strontium disodium ethylenediamine tetraacetate for alleviating hyper-sensitive dentin, an effective anti-caries amount of sodium monofluorophosphate and about 0.007 percent by weight, based on the total weight of the toothpaste, of monoammonium glycyrrhizinate, wherein said toothpaste is characterized by the substantial absence of substances which can replace strontium from said strontium disodium ethylenediamine tetraacetate.

6. A water-containing toothpaste comprising an effective amount of strontium disodium ethylenediamine tetraacetate for alleviating hyper-sensitive dentin, an effective anti-caries amount of sodium fluoride and from about 0.005 to about 0.5 percent by weight, based on the total weight of the toothpaste, of monoammonium glycyrrhizinate, wherein said toothpaste is characterized by the substantial absence of substances which can replace strontium from said strontium disodium ethylenediamine tetraacetate.

7. A water-containing toothpaste comprising an effective amount of strontium disodium ethylenediamine tetraacetate for alleviating hyper-sensitive dentin, an effective anti-caries amount of sodium fluoride and from 0.005 to 0.025 percent by weight, based on the total weight of the toothpaste, of monoammonium glycyrrhizinate, wherein said toothpaste is characterized by the substantial absence of substances which can replace strontium from said strontium disodium ethylenediamine tetraacetate.

8. A water-containing toothpaste comprising an effective amount of strontium disodium ethylenediamine tetraacetate for alleviating hyper-sensitive dentin, an effective anti-caries amount of sodium fluoride and from about 0.005 to about 0.0125 percent by weight, based on the total weight of the toothpaste, of monoammonium glycyrrhizinate, wherein said toothpaste is characterized by the substantial absence of substances which can replace strontium from said strontium disodium ethylenediamine tetraacetate.

9. A water-containing toothpaste comprising an effective amount of strontium disodium ethylenediamine tetraacetate for alleviating hyper-sensitive dentin, an effective anti-caries amount of sodium fluoride and about 0.007 percent by weight, based on the total weight of the toothpaste, of monoammonium glycyrrhizinate, wherein said toothpaste is characterized by the substantial absence of substances which can replace strontium from said strontium disodium ethylenediamine tetraacetate.

* * * * *